US00PP18684P2

(12) United States Plant Patent
Oudolf

(10) Patent No.: US PP18,684 P2
(45) Date of Patent: Apr. 1, 2008

(54) ***ECHINACEA* PLANT NAMED 'VIRGIN'**

(50) Latin Name: *Echinacea purpurea*
Varietal Denomination: Virgin

(75) Inventor: Petrus Hendricus Oudolf, De Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/637,855

(22) Filed: Dec. 12, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Echinacea* plant named 'Virgin', characterized by its compact and upright plant habit; moderately vigorous growth habit; freely flowering habit; large single inflorescences with white-colored ray florets; and strong peduncles that hold the inflorescences above the foliar plane.

2 Drawing Sheets

Botanical designation: *Echinacea purpurea.*
Cultivar denomination: 'Virgin'.

BACKGROUND OF THE INVENTION

The present invention relates to a new and distinct cultivar of *Echinacea* plant, botanically known as *Echinacea purpurea,* and hereinafter referred to by the name 'Virgin'.

The new *Echinacea* originated from an open-pollination of an unnamed selection of *Echinacea purpurea,* not patented, as the female, or seed, parent with an unknown selection of *Echinacea purpurea,* as the male, or pollen, parent. The new *Echinacea* was discovered and selected by the Inventor as a single flowering plant from within the progeny of the stated open-pollination grown in a controlled environment in Hummelo, The Netherlands in 2004.

Asexual reproduction of the new *Echinacea* by divisions in a controlled environment in Hummelo, The Netherlands since 2005, has shown that the unique features of this new *Echinacea* are stable and reproduced true to type in successive generations.

SUMMARY OF THE INVENTION

The cultivar Virgin has not been observed under all possible environmental conditions. The phenotype may vary somewhat with variations in environment such as temperature and light intensity, without, however, any variance in genotype.

The following traits have been repeatedly observed and are determined to be the unique characteristics of 'Virgin'. These characteristics in combination distinguish 'Virgin' as a new and distinct cultivar of *Echinacea:*

1. Compact and upright plant habit.
2. Moderately vigorous growth habit.
3. Freely flowering habit.
4. Large single inflorescences with white-colored ray florets.
5. Strong peduncles that hold the inflorescences above the foliar plane.

Compared to plants of the female parent selection, plants of the new *Echinacea* are more compact and are more freely flowering.

Plants of the new *Echinacea* can be compared to plants of the *Echinacea* cultivar Jade, disclosed in U.S. Plant Pat. No. 13,769. In side-by-side comparisons conducted in Lisserbroek, The Netherlands, plants of the new *Echinacea* differed from plants of the cultivar Jade primarily in number of rows of ray florets as plants of the cultivar Jade had a single row of ray florets. In addition, plants of the new *Echinacea* and the cultivar Jade differed slightly in ray floret coloration.

BRIEF DESCRIPTION OF THE PHOTOGRAPHS

The accompanying photographs illustrate the overall appearance of the new *Echinacea.* The photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of typical flowering plants of 'Virgin' grown in an outdoor nursery.

The photograph at the top of the second sheet is a close-up view of a typical inflorescence of 'Virgin'.

The photograph at the bottom of the second sheet is a close-up view of a typical leaf of 'Virgin'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Lisserbroek, The Netherlands during the summer in an outdoor nursery and under conditions and practices which approximate those generally used in commercial *Echinacea* production. During the production of the plants, day temperatures ranged from 18° C. to 35° C. and night temperatures ranged from 10° C. to 20° C. Measurements and numerical values represent averages for typical flowering plants. Plants were about two years old when the photographs and description were taken.

Botanical classification: *Echinacea purpurea* cultivar Virgin.

Parentage:

*Female parent.*—Unnamed selection of *Echinacea purpurea,* not patented.

*Male parent.*—Unknown selection of *Echinacea purpurea,* not patented.

Propagation:

*Type.*—By divisions.

*Time to produce a rooted young plant.*—About two months at 18° C. to 20° C.

*Root description.*—Fine, fibrous; light brown to white in color.

*Rooting habit.*—Freely branching; moderately dense.

Plant description:

*Plant form/growth habit.*—Compact, upright and uniform plant habit; inverted triangle; freely basal branching with inflorescences held above the foliage on strong peduncles. Moderately vigorous growth habit.

*Plant height.*—About 71.8 cm.

*Plant diameter or spread.*—About 55.3 cm.

*Lateral branches.*—Length: About 66.7 cm. Diameter: About 8 mm. Internode length: About 7.5 cm. Aspect: Mostly upright. Strength: Strong. Texture: Densely pubescent; rough. Color: 144A.

Foliage description:

*Arrangement.*—Alternate, simple; sessile.

*Length.*—About 11.3 cm.

*Width.*—About 4.9 cm.

*Shape.*—Narrowly ovate to ovate.

*Apex.*—Acute.

*Base.*—Attenuate.

*Margin.*—Irregularly serrate; undulate.

*Texture, upper and lower surfaces.*—Densely pubescent; rough.

*Venation pattern.*—Pinnate.

*Color.*—Developing foliage, upper surface: 137A. Developing foliage, lower surface: 138A to 138B. Fully expanded foliage, upper surface: 137A to 139A; venation, 145B. Fully expanded foliage, lower surface: 137C to 137D; venation, 145C to 145D.

Inflorescence description:

*Appearance.*—Rotate single inflorescence form with ray and disc florets. Inflorescences positioned above the foliage on strong peduncles. Inflorescences face upright. Freely flowering habit; about seven inflorescences develop per lateral branch. Inflorescences not persistent.

*Fragrance.*—Faint; sweet.

*Time to flower.*—Plants flower continuously from late June to mid-September in The Netherlands.

*Post-production longevity.*—Inflorescences maintain good substance for about three weeks on the plant.

*Inflorescence bud.*—Height: About 2.4 cm. Diameter: About 2.9 cm. Shape: Oblate. Color: 143A.

*Inflorescence size.*—Diameter: About 10.7 cm. Depth (height): About 5.1 cm. Disc diameter: About 5.1 cm. Receptacle height: About 2.5 cm. Receptacle diameter: About 2.3 cm.

*Ray florets.*—Length: About 4.9 cm. Width: About 1.1 cm. Shape: Oblanceolate. Apex: Emarginate to praemorse. Base: Cuneate. Texture, upper and lower surfaces: Smooth, glabrous; ribbed lengthwise. Number of ray florets per inflorescence: About 39 arranged in two whorls. Color: When opening, upper surface: 150D. When opening, lower surface: 150C to 150D. Fully opened, upper surface: Between 150D and 157A; color becoming closer to 150D with development. Fully opened, lower surface: 150D; color becoming closer to 144B with development.

*Disc florets.*—Shape: Tubular; apex dentate. Length: About 1.1 cm. Diameter: About 1 mm. Number of disc florets per inflorescence: About 500. Texture: Smooth, glabrous. Color: Immature: 144A; towards the base, 145C. Mature: 144A; towards the base, 145C.

*Receptacle spines.*—Quantity: One per disc floret. Length: About 1.5 cm. Width: About 1 cm. Shape: Acicular. Apex: Sharply acute. Color: Apex: 17A. Mid-section: 144A to 144C. Base: 145D.

*Phyllaries.*—Quantity per inflorescence: About 100 in about four whorls. Length: About 9 mm. Width: About 3 mm. Shape: Lanceolate. Apex: Acute. Base: Cuneate. Margin: Entire. Texture, upper surface: Smooth, glabrous. Texture, lower surface: Densely pubescent. Color, upper surface: 137A; towards the base, 137C. Color, lower surface: 137A.

*Peduncles.*—Length: About 23.9 cm. Diameter: About 6 mm. Strength: Strong. Aspect: Mostly upright. Texture: Densely pubescent; slight rough. Color: 144B.

*Reproductive organs.*—Androecium: Quantity per disc floret: About five. Filament length: About 7 mm. Filament color: 146A. Anther shape: Linear. Anther length: About 1 mm. Anther color: 146B to 146C. Pollen amount: Moderate. Pollen color: 13A. Gynoecium: Pistil length: About 7 mm. Stigma shape: Cleft; reflexed. Stigma color: 151A. Style length: About 4 mm. Style color: 145C. Ovary color: 157D. Seeds/fruits: Seed and fruit development have not been observed.

Disease/pest resistance: Plants of the new *Echinacea* have not been shown to be resistant to pathogens and pests common to *Echinacea.*

Garden performance: Plants of the new *Echinacea* have exhibited good tolerances to rain and wind and have been observed to be suitable for USDA Zones 3 or 4 to 9.

It is claimed:

1. A new and distinct *Echinacea* plant named 'Virgin' as illustrated and described.

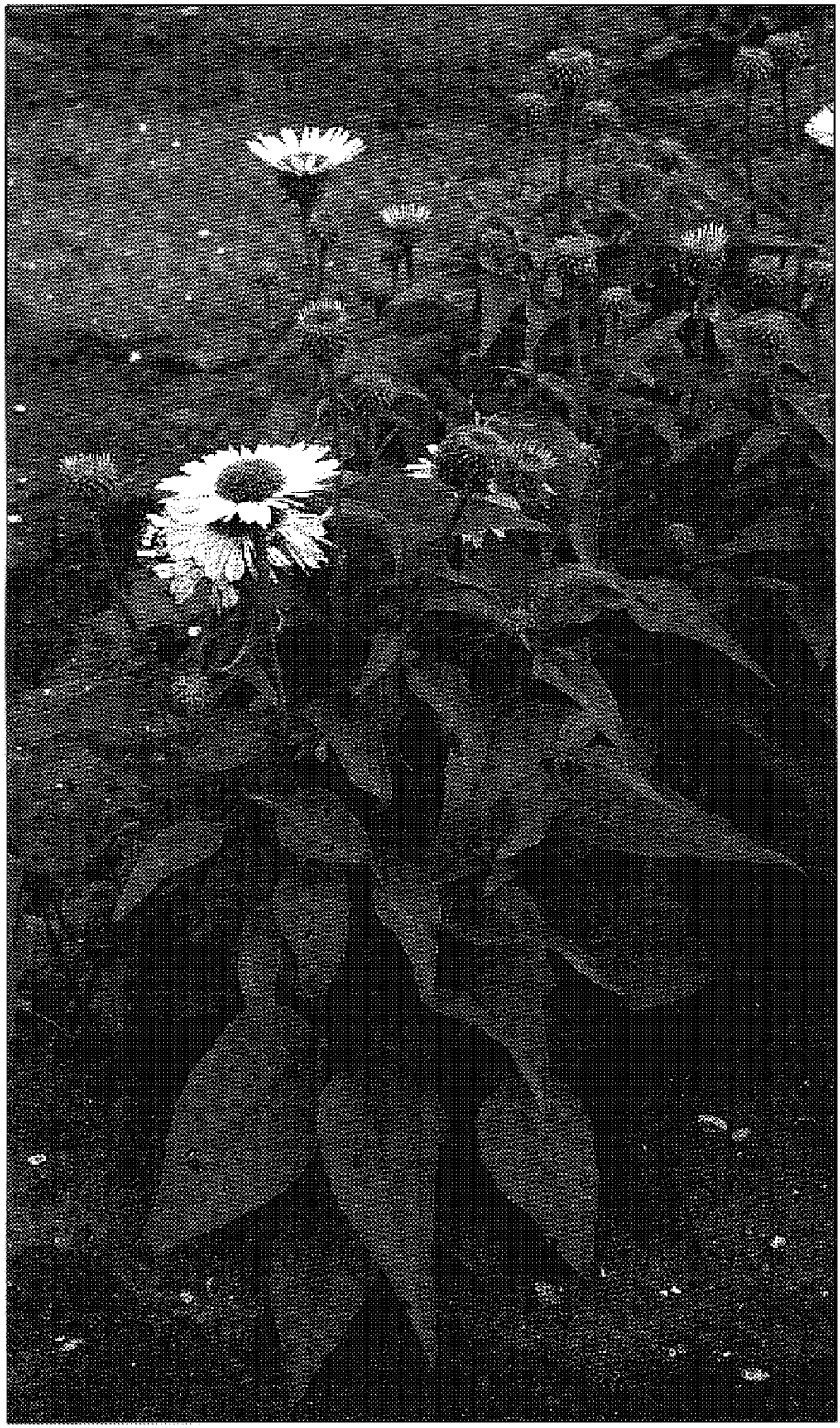

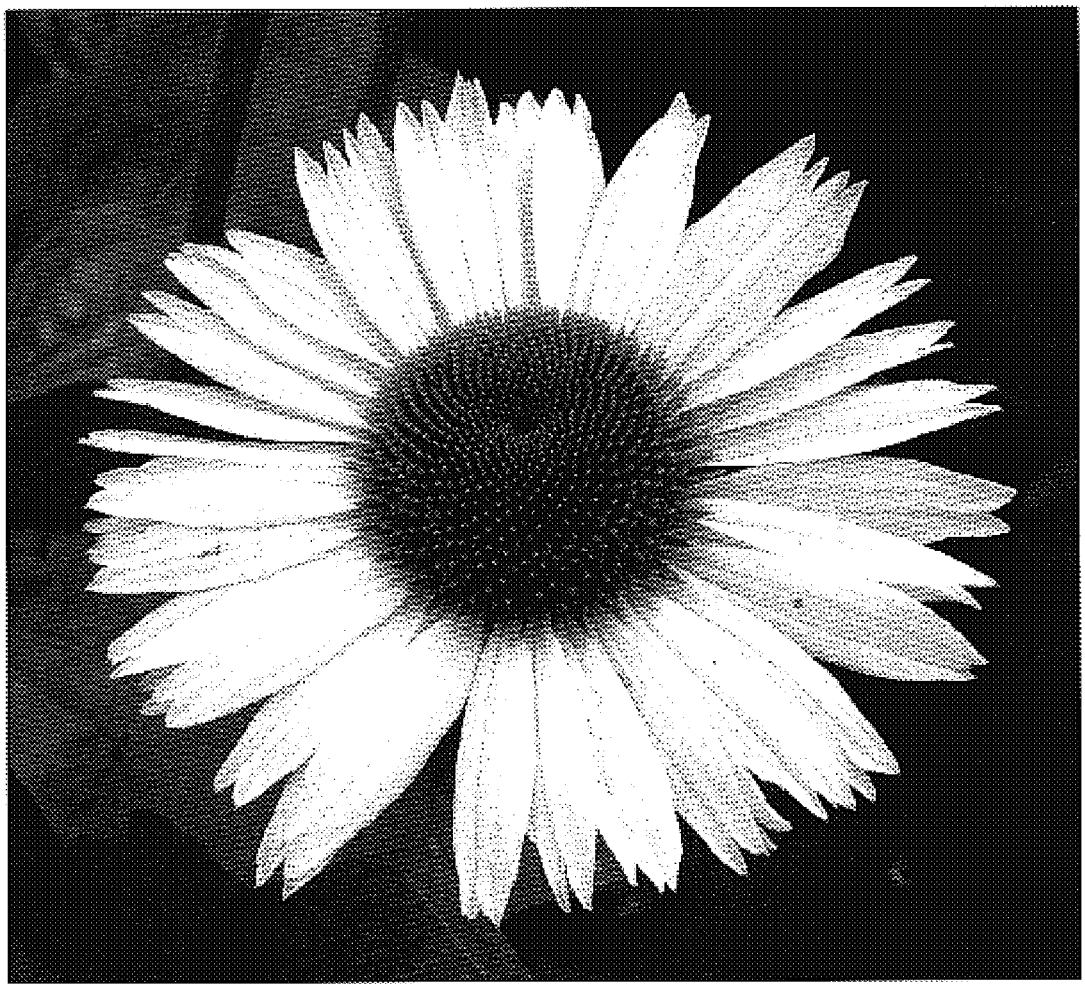
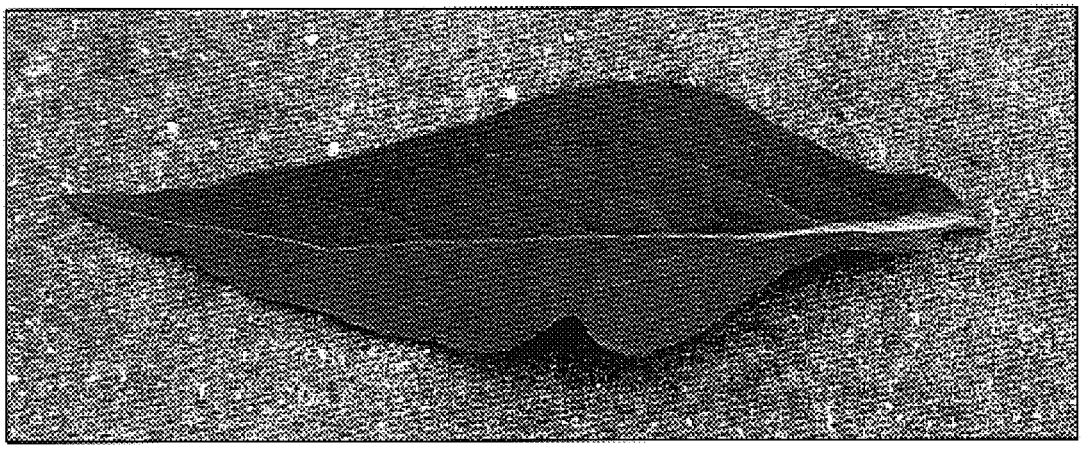

* * * * *